(12) United States Patent
Johnson

(10) Patent No.: US 6,280,415 B1
(45) Date of Patent: Aug. 28, 2001

(54) TISSUE TRACTION DEVICE

(76) Inventor: W. Dudley Johnson, N128 W17741 Holy Hill Rd., Germantown, WI (US) 53022

( * ) Notice: Subject to any disclaimer, the term of this patent is extended or adjusted under 35 U.S.C. 154(b) by 0 days.

(21) Appl. No.: 09/265,792

(22) Filed: Mar. 10, 1999

(51) Int. Cl.$^7$ .................................................. A61M 1/00
(52) U.S. Cl. .................. 604/118; 604/514; 604/264; 604/268; 604/902; 600/579; 433/91
(58) Field of Search .................. 604/48, 514, 93.01, 604/118, 119, 173, 176, 264, 268, 275, 523, 540, 544, 902, 35, 284, 30, 27, 28; 606/123, 162; 600/565, 156, 158, 576–579; 433/91, 95

(56) References Cited

U.S. PATENT DOCUMENTS

| | | | |
|---|---|---|---|
| 3,902,494 | * 9/1975 | Haberlen et al. | 128/275 |
| 3,965,901 | 6/1976 | Penny et al. | 128/276 |
| 4,049,000 | 9/1977 | Williams | 128/276 |
| 4,158,916 | * 6/1979 | Adler | 32/33 |
| 4,198,958 | 4/1980 | Utsugi | 128/5 |
| 4,265,621 | * 5/1981 | McVey | 433/91 |
| 4,306,561 | 12/1981 | de Medinaceli | 128/303.13 |
| 4,487,600 | 12/1984 | Brownlie et al. | 604/35 |
| 4,684,362 | * 8/1987 | Holt | 604/54 |
| 4,935,006 | * 6/1990 | Hasson | 604/43 |
| 4,955,896 | 9/1990 | Freeman | 606/210 |
| 5,181,916 | * 1/1993 | Reynolds et al. | 606/16 |
| 5,213,110 | 5/1993 | Kedem et al. | 128/754 |
| 5,242,387 | 9/1993 | Loughlin | 604/43 |
| 5,269,768 | 12/1993 | Cheung | 604/248 |
| 5,306,234 | 4/1994 | Johnson | 604/49 |
| 5,314,406 | 5/1994 | Arias et al. | 604/21 |
| 5,348,555 | 9/1994 | Zinnanti | 606/49 |
| 5,417,709 | 5/1995 | Slater | 606/205 |
| 5,419,769 | 5/1995 | Devlin et al. | 604/119 |
| 5,437,651 | 8/1995 | Todd et al. | 604/313 |
| 5,599,304 | * 2/1997 | Shaari | 604/94 |
| 5,713,849 | 2/1998 | Bosma et al. | 604/28 |
| 5,727,569 | 3/1998 | Benetti et al. | 128/898 |
| 5,975,897 | * 11/1999 | Propp et al. | 433/91 |

* cited by examiner

Primary Examiner—Richard K. Seidel
Assistant Examiner—Cris Rodriguez
(74) Attorney, Agent, or Firm—Philip G. Meyers; Philip G. Meyers Intellectual Property Law, P.C.

(57) ABSTRACT

A tissue traction device according to the invention includes an elongated tube defining a vacuum passageway, which tube has a proximate end defining a first opening, a distal end defining a second opening, and a third opening between the ends. A shield covers the distal end of the tube, the shield having a plurality of openings providing communication between the vacuum passageway and an exterior surface of the shield. The shield prevents the tissue from being pulled deep into the tube, thereby protecting the tissue from damage. Each of the openings having a cross-sectional area smaller than the cross-sectional area of the vacuum passageway. The tube and shield are configured for use in surgery, such that when suction is applied to one of the first and third openings, the level of suction through the second opening can be controlled by varying the extent to which the other of the first and third openings is uncovered, whereby the suction causes the shield to selectively hold tissue against the shield. The invention provides an apparatus and method for gently holding, moving and exposing soft tissue without clamping, and is particularly adapted for use through an endoscopic port, either in the chest or abdomen.

19 Claims, 2 Drawing Sheets

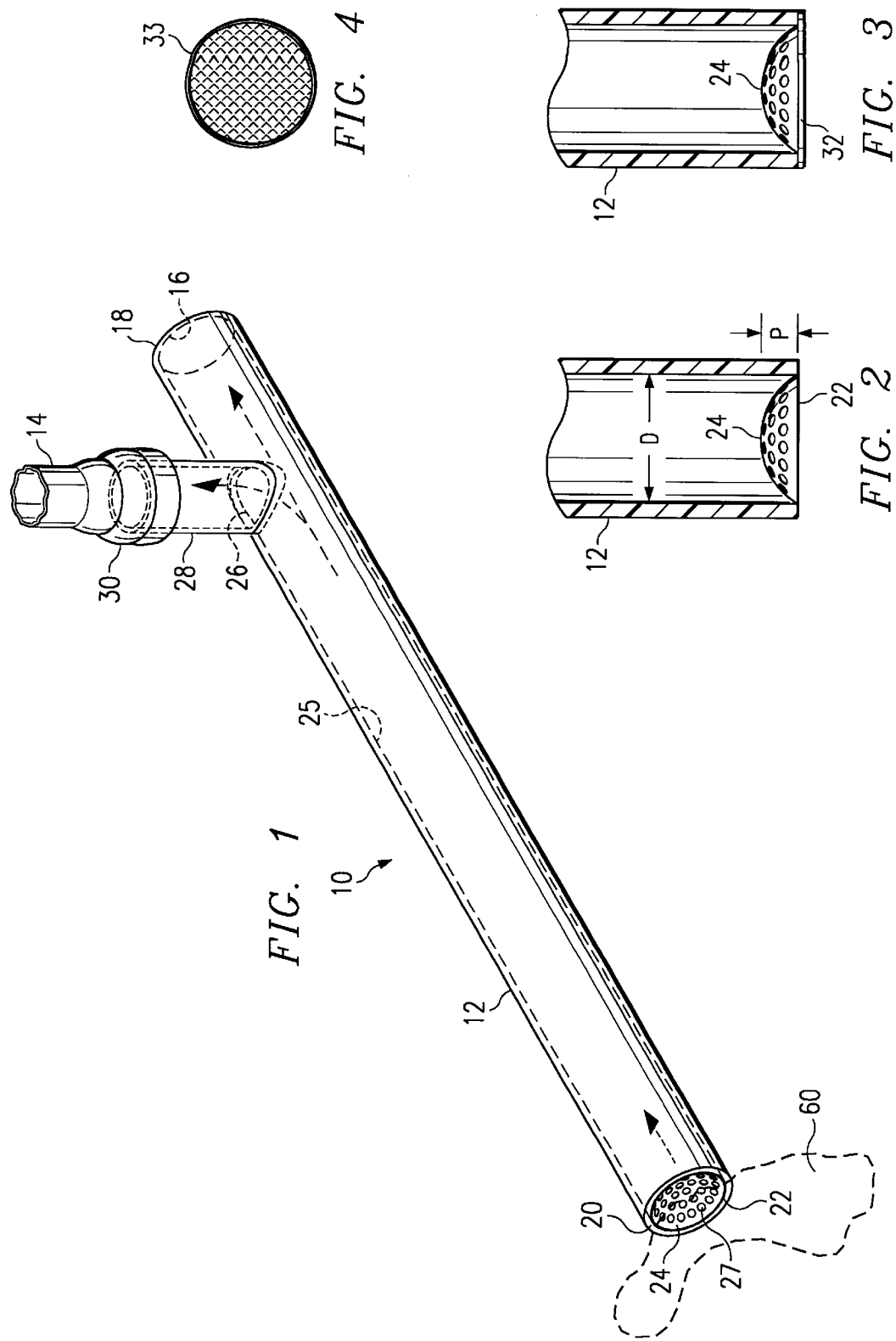

TISSUE TRACTION DEVICE

TECHNICAL FIELD

The invention relates to surgical devices and procedures, in particular to a tissue traction device designed to hold, move and expose soft tissue during surgical procedures.

BACKGROUND OF THE INVENTION

During surgery, tissues often have to be mobilized and displaced in order to obtain optimal exposure of the affected area or organ. In traditional surgical procedures, the affected organ or area is exposed using a relatively large incision, typically in the chest or abdomen. For example, in many traditional open heart surgical procedures, the chest cavity is opened and the ribs retracted to expose the heart. When a large incision is made, exposure of the organ or tissue to be operated upon is seldom a critical factor, i.e., it is comparatively easy to immobilize or displace intervening tissues to expose the target area. If an artery ruptures or a similar urgent problem arises that requires access to the organ, the organ is already exposed to a sufficient extent to deal with the complication.

In recent years, however, surgeons have turned to endoscopic techniques to reduce the trauma associated with traditional surgical methods. In particular, methods have been proposed for performing operations on heart tissues without opening the chest. See Johnson U.S. Pat. No. 5,306,234. Methods have also been proposed for performing bypass operations without opening the chest, as described in Sterman et al. U.S. Pat. Nos. 5,571,215 and 5,452,733. In endoscopic surgery, in which a relatively small incision is made and an observation device is inserted into the body and relied upon to guide the surgery, effective exposure of the target tissue or organ becomes more critical.

According to conventional practice, after an incision is made, soft tissues such as bowel or lung are displaced with broad, flat retractors. In some cases, traction is required to retain the tissue in order to obtain exposure of the organ or area where the surgery is to be performed. Retraction is usually accomplished by clamping the tissue (i.e., bowel, gall bladder, atrium) with a "a traumatic clamp". The clamp is then used to pull the tissue in whatever direction is necessary to obtain the required exposure. No clamp is, however, truly a traumatic. Crushing a piece of tissue always causes at least mild tissue damage. If the tissue to be clamped and/or retracted is inflamed or tense, clamping is even more likely to result in tissue damage, including perforation of the tissue. Thus, there exists a need for an improved device and method for mobilizing and displacing soft tissue during surgical procedures, in particular during endoscopic surgical procedures, that provides traction without the trauma associated with traditional surgical clamps.

A device according to the invention that meets this need uses suction as described in detail hereafter to mobilize and displace soft tissue. Suction applied through tubular devices inserted into the body has long been used as a means of removing unwanted fluids during surgery. Benetti et al. U.S. Pat. No. 5,727,569 describes devices which use negative pressure during open heart surgery to immobilize cardiac tissue during surgery which include a ring-shaped device and a hand-held device resembling a pair of tongs. A need nonetheless persists for a device for manipulating soft tissue that is simple, easy to use and control, and which can be used in endoscopic surgery.

SUMMARY OF THE INVENTION

A tissue traction device according to the invention includes an elongated tube defining a vacuum passageway, which tube has a proximate end defining a first opening, a distal end defining a second opening, and a third opening between the ends. A shield is held within the distal end of the tube, the shield having a plurality of openings providing communication between the vacuum passageway and an exterior surface of the shield. The shield prevents the tissue from being pulled deep into the tube, thereby protecting the tissue from damage. Each of the openings has a cross-sectional area smaller than the cross-sectional area of the vacuum passageway. The tube and shield are configured for use in surgery, such that when suction is applied to one of the first and third openings, the level of suction through the second opening can be controlled by varying the extent to which the other of the first and third openings is uncovered, whereby the suction causes the shield to selectively hold tissue against the shield. In one embodiment, the proximate end of the tube defines an opening adapted to be manually blocked with a human digit such as a thumb or finger. In a further embodiment, a tube with several interchangeable tips is provided so that the traction device may be used at a variety of angles.

A method for manipulating tissue using the tissue traction device of the invention includes the steps of:

(a) applying the distal end of the tube to the tissue to be manipulated so that the tissue is in contact with the shield;

(b) applying suction to the tube through one of the second and third openings so that suction is applied to the tissue though the holes in the shield and the tissue is held against the shield by the suction;

(c) manipulating the tissue; and (d) releasing the tissue by decreasing the suction applied through the tube. Prior to step (a), according to a further aspect of the invention, the tube is inserted through a small opening into the body to an internal target site which has not been exposed, for example, by open surgery. Following step (c), when the target tissue is exposed truly a traumatically, an endoscopic operation may then be carried using the device of the invention to help manipulate tissues as needed. The suction applied to the tissue may be manually controlled by blocking and unblocking one of the first and third openings while the suction is applied through the other of the first and third openings, and/or by using a suction control device remote from the tissue traction device, such as a wall valve. When the operation is completed, the tube is removed from the target site by withdrawing it out of the body. These and other aspects of the invention are discussed in the detailed description which follows.

BRIEF DESCRIPTION OF THE DRAWINGS

Reference is now made to the detailed description of the invention along with the accompanying figures in which corresponding numerals in the different figures refer to corresponding parts, and in which:

FIG. 1 is a perspective view of a tissue traction device according to the invention;

FIG. 2 is a partial side view of the distal end of the device shown in FIG. 1;

FIG. 3 is a view similar to FIG. 2 of an alternative means of securing the shield to the tube;

FIG. 4 is front view of an alternative form of the shield used in the invention;

DETAILED DESCRIPTION

Figure 5:
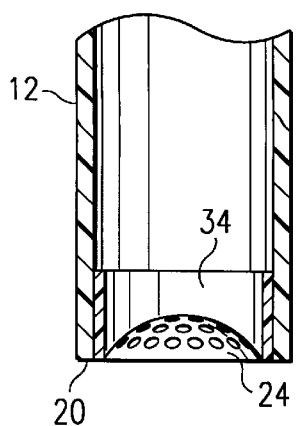
FIG. 5 is a partial side view of a second alternative form of the shield used in the invention.

Referring now to FIG. 1, a tissue traction device 10 of the present invention includes an elongated hollow tube 12 having a proximal end 18 and distal end 20 and defining a central vacuum passageway 25 extending the length of the tube. Proximal end 18 terminates in a round first opening 16 which, as will be explained in greater detail below, allows for manual control of the negative pressure inside tube 12. Distal end 20 terminates in a round second opening 22 having a diameter the same as that of passageway 25. In contrast to many other known surgical devices that apply suction through tubes, passage 25 of tube 12 is preferably open and free of other devices or structures, for example, wires to insert into the body, or the like.

Tube 12 is preferably formed from metal such as stainless steel or a plastic such as nylon, surlyn, polypropylene, or polyethylene and should be rigid enough to prevent unwanted movement during surgery. The length of tube 12 is normally in the range of approximately 20 to 40 cm, especially about 30 cm, and may vary outside this range depending upon the particular application or procedure for which device 10 is to be used. The wall thickness and outer diameter of tube 12 may also vary depending upon the particular application. For most applications, the outer diameter of tube 12 will be in the range of from about 5 to 20 mm, with a wall thickness sufficient to ensure rigidity under surgical conditions. Since tube 12 will be inserted through conventional trocar ports or sheaths, sizes corresponding to the port openings (e.g., 10, 12, 14 mm) are most suitable. The diameter of tube 12 and the corresponding surface area of shield 24 should be sufficient to distribute the suction over a sufficiently wide area that tissue damage is minimized and a sufficient hold on the tissue or organ to be mobilized is achieved.

Tissue traction device 10 has a round third opening 26 which opens onto a branch conduit 28 which is preferably integrally formed as part of tube 12. Branch conduit 28 preferably has the same or slightly smaller diameter than tube 12 and a length sufficient to permit attachment to a rubber or plastic hose 14 by suitable means such as a flared end coupling 30. Conduit 28 and opening 26 are preferably located near to proximal end 18 so that a major portion of the length of tube 12 can be inserted into the body as described hereafter. Hose 14 is connected to a conventional medical vacuum source (not shown) and communicates with tube 12 to provide a negative pressure to passageway 25. A vacuum source providing a negative pressure of about 18 inches of mercury is suitable.

Perforated shield 24 may be formed integrally with the tube 12 or installed as a separate piece, in which case it may be secured in opening 22 by any suitable means, such as an adhesive, welding or a fastener as noted in connection with FIG. 3. As illustrated, shield 24 covers distal opening 22 of tube 12. Holes 27 allow communication between the inside of tube 12 and the outside of the shield. As shown, each hole 27 is substantially smaller (half or less) in cross-sectional area than the cross-sectional area of the vacuum passageway 25. The diameter of each hole 27 preferably ranges from about 1 to 2 mm. Further, while the holes 27 illustrated are circular, other shapes could be used, for example, holes 27 could be rectangular or oblong slots.

Shield 24 may be flat but, as best illustrated in FIGS. 2 and 3, shield 24 preferably forms a shallow rounded cavity in order to minimize surface area for gripping soft tissue. A shallow concave shape is most preferred wherein the center of shield 24 is recessed from opening 22 by a distance P in the lengthwise direction of tube 12, which distance P is half or less of the diameter D of shield 24. In the embodiment of FIG. 3, a press-fitted or threaded, metal or plastic rim 32 is used to secure shield 24 by its edge so that shield 24 can be reused. An alternative shield 33 may be formed using a metal or plastic porous mesh or screen as shown in FIG. 4 with individual openings that may well be finer than the size of holes 27.

Figure 6:
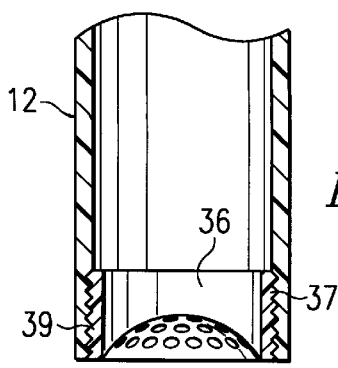
FIG. 6 is a partial side view of a third alternative form of the shield used in the invention.

A variety of configurations may be used to secure shield 24. FIG. 5 shows a further alternative embodiment wherein shield 24 is part of a cup-shaped insert 34 that is press-fitted into opening 22 and resiliently engages the inside of tube 12, so that it does not slip in or out of tube 12 during use. In FIG. 6, a shield insert 36 has external threads 37 that engage internal threads 39 on the inside of tube 12 adjacent opening 22.

Figure 7:
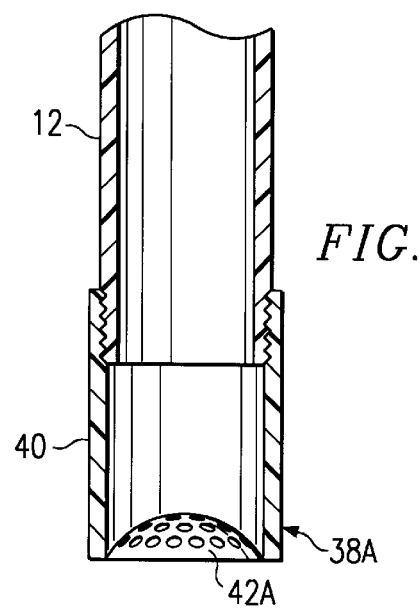
FIG. 7 is a partial side view of a tissue traction device according to the invention with a removable tip.
Figure 8:
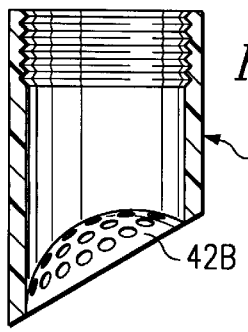
FIGS. 8 and 9 are partial side views of additional removable tips usable with the embodiment of FIG. 7.
Figure 9:
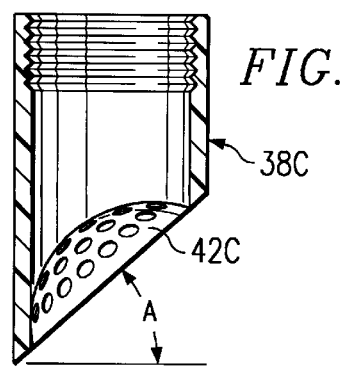

FIGS. 7–9 illustrate a further embodiment similar to that of FIG. 6, except that a modified shield insert 38A has a greater length so that a tubular front portion 40 projects from opening 22 and effectively acts as a removable tip. Additional removable tips 38B and 38C may be provided wherein the end face 42B, 42C defines a different acute angle A relative to the lengthwise axis of tube 12. The shield portions of tips 38B, 38C remain inwardly concave but conform to the angled end face as shown. The surgeon selects and installs a tip 38A–38C that best suits the angle at which the device 10 will be inserted during surgery. Angle A may, for example, vary from 0 to 60 degrees. In the alternative, a set of different tubes 12 can be produced each having an opening 22 modified to provide a different angle A.

As noted above, during an endoscopic surgical procedure, it may become necessary to move and/or hold soft tissue in order to expose the affected organ or area The tube 12 is inserted through the endoscopic incision, which may be made by conventional or laser surgery, and positioned against soft tissue 60, such as bowel, lung or atrium, to be held or moved as illustrated in FIG. 1. A trocar sheath is preferably inserted into the incision to aid in insertion and removal of device 10. Generally, tissue traction device 10 is positioned with the aid of an endoscope (not shown) at the desired location. When device 10 is positioned at the desired location with the shield 24 adjacent to the soft tissue 60 to be held and manipulated. Vacuum is applied to the tube 12 through hose 14. Shield 24 and tube 12 define a concave cavity adjacent to soft tissue 60. The suction is controlled during the operation by opening and closing opening 16 at the proximate end 18 of tube 12 by covering it with a digit, i.e., finger or thumb. Partial blocking of opening 16 may be used to control the amount of suction applied to tissue 60, but this is difficult to do in practice, and thus it is preferred to vary the amount of suction desired by other means, such as a wall valve provided with a pressure gauge, using end 18 mainly for turning suction on and off as desired. Shield 24 prevents the soft tissue 60 from being pulled deeper into the tube, thereby protecting the soft tissue from damage, and the degree and duration of aspiration is controlled to avoid drying the tissue excessively.

At this point, soft tissue 60 is manipulated as desired during the course of the operation. Tissue 60 may be the target tissue to be operated on, or a tissue which must be moved aside or immobilized during an operation on an adjoining or underlying structure. To release the soft tissue 60 from the tissue traction device, the user removes his or her thumb or finger from opening 16 at the proximate end 18 of tube 12, thereby releasing the vacuum.

The present invention thus provides an apparatus and method for gently holding, moving and exposing soft tissue without clamping, and is particularly adapted for use through an endoscopic port, either in the chest or abdomen. Although various embodiments of the invention have been illustrated in the accompanying drawing and described in the foregoing detailed description, it will be understood that the invention is not limited to the embodiments disclosed but, as will be appreciated by those skilled in the art, is susceptible to numerous modifications and variations without departing from the spirit and scope of the invention as hereof claimed.

What is claimed is:

1. A tissue traction device, comprising:
   an elongated hollow tube defining a vacuum passageway, which tube has a proximate end defining a first opening, a distal end defining a second opening, and a third opening between the ends, the tube further comprising a branch conduit which extends from the third opening; and
   a shield covering the distal end of the tube, the shield having holes therein providing communication between the vacuum passageway and an exterior surface of the shield, each of the holes having a cross-sectional area smaller than the cross-sectional area of the vacuum passageway;
   wherein the tube and shield are configured for use in surgery, such that when suction is applied to one of the first and third openings, the level of suction through the second opening can be controlled by opening and closing the other of the first and third openings, whereby the suction causes the shield to hold and release tissue against the shield.

2. The device of claim 1, wherein the branch conduit is tubular and extends from a sidewall of the tube.

3. The device of claim 2, further comprising a vacuum hose and means for attaching the vacuum hose to the branch conduit.

4. The device of claim 2, wherein the diameter of the tube is such that a human digit may be used to cover up the first opening.

5. The device of claim 2, wherein the tube is made of rigid plastic, has a length in the range of from about 20 to 40 cm, and an outer diameter in the range of about 5 to 20 mm.

6. The device of claim 2, wherein the tube is made of metal, has a length in the range of from about 20 to 40 cm, and an outer diameter in the range of about 5 to 20 mm.

7. The device of claim 1, wherein the shield comprises a porous mesh.

8. The device of claim 1, wherein the tube has an interior which is clear of devices other than the shield.

9. The device of claim 1, wherein the tube and branch conduit are integrally formed.

10. The device of claim 1, further comprising means for removably fastening the shield to the distal end of the tube.

11. A tissue traction device, comprising:
    an elongated hollow tube defining a vacuum passageway, which tube has a proximate end defining a first opening, a distal end defining a second opening, and a third opening between the ends; and
    a shield covering the distal end of the tube, the shield having holes therein providing communication between the vacuum passageway and an exterior surface of the shield, each of the holes having a cross-sectional area smaller than the cross-sectional area of the vacuum passageway wherein the has a concave shape and is recessed inside the distal end the tube;
    wherein the tube and shield are configured for use in surgery, such that when suction is applied to one of the first and third openings, the level of suction through the second opening can be controlled by opening and closing the other of the first and third openings, whereby the suction causes the shield to hold and release tissue against the shield.

12. A tissue traction device, comprising:
    an elongated hollow tube defining a vacuum passageway, which tube has a proximate end defining a first opening, a distal end defining a second opening, and a third opening between the ends; and
    a shield covering the distal end of the tube; the shield having holes therein providing communication between the vacuum passageway and an exterior surface of the shield, each of the holes having a croos-sectional area smaller than the cross-sectinal area of the vacuum passageway;
    wherein the tube and shield are configured for use in surgery, such that when suction is applied to one of the first and third openings, the level of suction through the second opening can be controlled by opening and closing the other of the first and third openings, wherby the suction causes the shield to hold and release tissue against the shield;
    a vacuum hose; and
    means for attaching the vacuum hose to one of the first or third openings.

13. A method for manipulating tissue using a tissue traction device, which tissue traction device comprises an elongated hollow tube defining a cacuum passageway, which tube has a proximate end defining a first opening, a distal defining a second opening, and a third opening between the ends, and a shield covering the distal end of the tube, the shield having holes therein providing communication between the vacuum passageway and an exterior surface of the shield, each of the holes having a cross-sectional area smaller than the cross-sectional area of the vacuum passageway, wherein the tube and shield are configured for use in surgery, such that when suction is applied to one of the first and third openings, the level of suction through the second opening can be controlled by varying the extent to which the other of the first and third openings is uncovered, whereby the suction causes the shield to selectively hold tissue against the shield, comprising the steps of:
    (a) applying the distal end of the tube to the tissue to be manipulated so that the tissue is in contact with the shield;
    (b) applying suction to the tube through one of the first and third openings so that suction is applied to the tissue through the holes in the shield and the tissue is held against the shield by the suction;
    (c) manipulating the tissue; and
    (d) releasing the tissue by decreasing by decreasing the suction applied through the tube.

14. The method of claim 13, further comprising the additional steps of:
    prior to step (a), inserting the tube into a human body to an internal target site which needs to be more adequately exposed; and following step (d), removing the tube from the target site by withdrawing it out of the human body.

15. The method of claim 14, further comprising performing an endoscopic surgical procedure which is facilitated by step (c).

16. The method of claim 13, further comprising manually controlling suction force applied to the tissue by blocking and unblocking one of the first and third openings while the suction is applied through the other of the first and third openings.

17. The method of claim 16, wherein the tube of the traction device includes a branch conduit which extends from the third opening, and step (b) further comprises applying suction from a vacuum source through a hose attached to the branch conduit.

18. The method of claim 17, wherein the step of manually controlling suction force applied to the tissue comprises fully of partially blocking and unblocking the first opening.

19. The method of claim 17, further comprising controlling the degree of suction applied to the target tissue using a suction control device remote from the tissue traction device.

\* \* \* \* \*